United States Patent [19]
Horn et al.

[11] 4,257,950
[45] Mar. 24, 1981

[54] CONTINUOUS PREPARATION OF ε-CAPROLACTAM BY BECKMANN REARRANGEMENT

[75] Inventors: Peter Horn, Hirschberg; Otto-Alfred Grosskinsky, Ludwigshafen; Richard Thoma, Battenberg; Hugo Fuchs, Ludwigshafen, all of Fed. Rep. of Germany

[73] Assignee: BASF Aktiengesellschaft, Fed. Rep. of Germany

[21] Appl. No.: 79,329

[22] Filed: Sep. 27, 1979

[30] Foreign Application Priority Data

Oct. 16, 1978 [DE] Fed. Rep. of Germany ....... 2845019

[51] Int. Cl.$^3$ .......................................... C07D 201/04
[52] U.S. Cl. .............................................. 260/239.3 A
[58] Field of Search ................................ 260/239.3 A

[56] References Cited

U.S. PATENT DOCUMENTS

| 2,249,177 | 7/1941 | Schlack | 260/239.3 A |
| 2,573,374 | 10/1951 | Wichterle | 260/239.3 A |

FOREIGN PATENT DOCUMENTS

| 860357 | 12/1952 | Fed. Rep. of Germany ... 260/239.3 A |
| 2739614 | 3/1978 | Fed. Rep. of Germany ... 260/239.3 A |
| 267114 | 6/1950 | Switzerland ...................... 260/239.3 A |
| 900801 | 7/1962 | United Kingdom ............. 260/239.3 A |

*Primary Examiner*—John D. Randolph
*Assistant Examiner*—Robert T. Bond
*Attorney, Agent, or Firm*—Keil & Witherspoon

[57] ABSTRACT

A process for the continuous preparation of ε-caprolactam by Beckmann rearrangement of cyclohexanone-oxime, dissolved in a solvent which is inert toward oleum and is immiscible with oleum and water, at an elevated temperature, with removal of the heat of rearrangement by evaporation of the solvent, wherein oleum containing caprolactam is circulated successively through a conveying zone, a mixing zone, a boiling zone and a separating zone, upstream of the conveying zone oleum is added at the rate at which it is consumed, in the mixing zone cyclohexanone-oxime dissolved in solvent is added under turbulent conditions, in the boiling zone the heat of rearrangement is removed in a conventional manner by evaporating the solvent and recycling the condensate, and in the separating zone the reaction mixture is separated into a solvent phase, from which solvent is withdrawn at the rate at which the phase is formed, and a caprolactam-containing oleum phase, which is removed at the rate at which it is formed.

6 Claims, 1 Drawing Figure

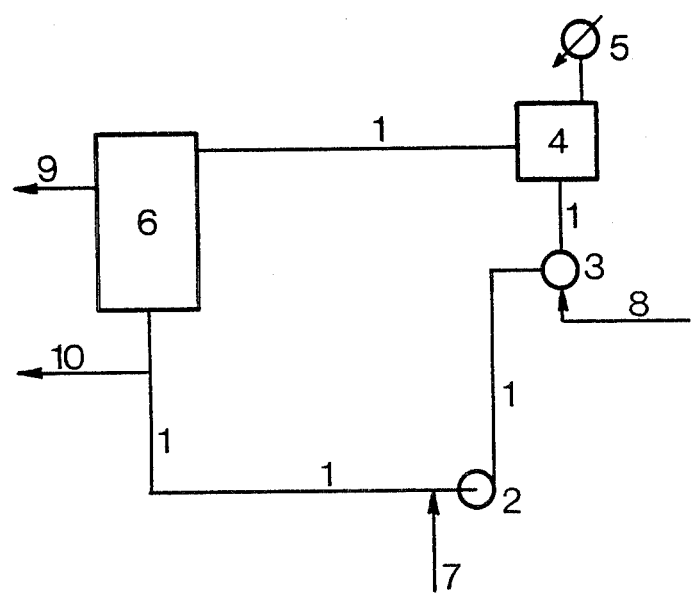

CONTINUOUS PREPARATION OF ε-CAPROLACTAM BY BECKMANN REARRANGEMENT

The present invention relates to a process for the continuous preparation of ε-caprolactam by Beckmann rearrangement of cyclohexanone-oxime which is dissolved in a solvent which is inert towards oleum and immiscible with oleum and water, at an elevated temperature, with removal of the heat of rearrangement by evaporation of the solvent.

German Pat. No. 860,357 has disclosed a process for the rearrangement of cyclohexanone-oxime, dissolved in methylene chloride, in which the cyclohexanone-oxime solution is conveyed in counter-current to sulfuric acid. Similarly, Swiss Pat. No. 267,114 discloses a process for the rearrangement of cyclohexanone-oxime, in which a cyclohexanone-oxime solution and sulfuric acid are passed simultaneously into a reaction vessel and the heat of reaction is removed by evaporation of the solvent. Neither process has hitherto found acceptance in industry, since both suffer from diverse shortcomings. The disadvantages of the processes described are discussed in detail as prior art in British Pat. No. 900,801. For example, the processes give products of relatively poor quality, and suffer from considerable technical shortcomings, since high-speed stirrers and baffles must be employed, and high-speed stirrers entail high energy costs and high maintenance costs. Circulatory processes for the Beckmann rearrangement of cyclohexanone-oxime have also already been employed (German Laid-Open Application DOS No. 2,739,614). Such processes have the disadvantage that because of the use of external cooling, local overheating cannot be avoided. This leads to a reduction in yield and to the formation of undesired by-products which can only be removed with difficulty.

It is an object of the invention to provide a method of rearrangement of cyclohexanone-oxime in solution which is easy to carry out industrially and produces only very small amounts of impurities which are difficult to remove.

We have found that this object is achieved by a process for the continuous preparation of ε-caprolactam by Beckmann rearrangement of cyclohexanone-oxime, dissolved in a solvent which is inert toward oleum and is immiscible with oleum and water, at an elevated temperature, with removal of the heat of rearrangement by evaporation of the solvent, wherein oleum containing caprolactam is circulated successively through a conveying zone, a mixing zone, a boiling zone and a separating zone, upstream of the conveying zone oleum is added at the rate at which it is consumed, in the mixing zone cyclohexanone-oxime dissolved in solvent is added under highly turbulent conditions, in the boiling zone the heat of rearrangement is removed in a conventional manner by evaporating the solvent and recycling the condensate, and in the separating zone the reaction mixture is separated into a solvent phase, from which solvent is withdrawn at the rate at which the phase is formed, and a caprolactam-containing oleum phase, which is removed at the rate at which it is formed.

The novel process has the advantage that no local overheating occurs and the heat of rearrangement is removed immediately. It has the further advantage that it is simple to carry out and can easily be scaled up to industrial operation. Furthermore, it has the advantage that it gives excellent yields and impurities which are difficult to remove are formed in smaller amount than hitherto.

According to the invention, caprolactam-containing oleum is circulated through a conveying zone, a mixing zone, a boiling zone and a separating zone. Upstream of the conveying zone, oleum is added at the rate at which it is consumed, and in the mixing zone cyclohexanone-oxime, dissolved in solvent, is introduced under high turbulence. In the boiling zone, downstream of the mixing zone, the heat of rearrangement is removed by evaporation of solvent, the condensate being recycled. In the separating zone, downstream of the boiling zone, the reaction mixture is separated into two phases, namely a solvent phase and a caprolactam-containing oleum phase. The solvent is removed from the solvent phase at the rate at which it arises, whilst caprolactam, dissolved in oleum, is removed from the caprolactam-containing oleum phase at the rate at which it is formed, and the residual caprolactam-containing oleum phase is recycled to the conveying zone after topping up with fresh oleum.

Advantageous solvents are cycloalkanes, preferably boiling at 50–110° C. Examples of suitable cycloalkanes are cyclopentane, cyclohexane, cycloheptane and mixtures of these. As a rule, a solution containing from 10 to 30 percent by volume of cyclohexanone-oxime in the said solvents is used. Such solutions are prepared, for example, by dissolving cyclohexanone-oxime, which still contains from 3 to 7% by weight of water from the process of preparation of the cyclohexanone-oxime. Advantageously, water is removed from the cyclohexanone-oxime solution before use, for example by decanting or azeotropic distillation.

The caprolactam-containing oleum in general contains from 40 to 60% by weight of caprolactam, especially from 46 to 53%.

Oleum for the purposes of the invention means sulfuric acid containing free sulfur trioxide. It goes without saying that the rapidly circulating liquid additionally contains dissolved caprolactam. Advantageously, the content of free $SO_3$ in the circulating liquid, comprising oleum and caprolactam, is kept at from 5 to 15, especially from 8 to 14, % by weight.

Oleum is introduced upstream of the conveying zone. For the purposes of the invention, the conveying zone consists of pumps suitable for the medium described, for example the centrifugal pumps or piston pumps conventionally used in industry. Downstream of the conveying zone, the above solution of cyclohexanone-oxime in a solvent is introduced under high turbulence into a mixing zone. The high turbulence is advantageously achieved by introducing the cyclohexanone-oxime solution axially and radially through nozzle orifices under a pressure of from 5 to 25 bar, especially from 10 to 20 bar, into a mixing zone which narrows in the direction of flow, whilst the circulating caprolactam-containing oleum is introduced laterally into the mixing zone, at the level of the nozzle orifice. In this way, the turbulence caused achieves intimate mixing of the cyclohexanone-oxime solution with the oleum, and hence brings about a rapid reaction.

In a boiling zone which is advantageously directly downstream of the mixing zone and which is, for example, a vessel with appropriate cooling equipment, solvent is evaporated as a result of the generated heat of rearrangement, and the condensed vapors are recycled. This provides a simple method of rapidly removing the heat of rearrangement, so that at no point do superheating phenomena arise. Preferably, the reaction temperature is kept at from 60 to 110° C.; it can easily be regulated by means of the boiling point of the solvent used, for example by working under atmospheric, reduced or superatmospheric pressure. If cyclohexane, the preferred solvent, is used, a temperature of 80° C.±2° C. can be maintained at atmospheric pressure. This temperature can be varied by changing the pressure and hence the boiling point.

It has also proved advantageous to use a volume ratio of the total amount of oleum/caprolactam mixture circulated per unit time to the amount of cyclohexanoneoxime solution introduced of from 300:1 to 1:1, preferably from 100:1 to 3:1.

Downstream of the boiling zone, the reaction mixture is passed into a separating zone, where it separates into a solvent phase and a caprolactam-containing oleum phase. The solvent is withdrawn from the solvent phase at the rate at which it arises and is advantageously washed with water and then reused to dissolve cyclohexanone-oxime. Caprolactam-containing oleum is removed, from the caprolactam-containing oleum phase, at the rate at which it arises. The remaining amount of caprolactam-containing oleum is recycled to the conveying zone, after topping up with oleum. The residence time in the separating zone is as a rule from 10 to 30 minutes, whilst the mean residence time in the total circulatory system is from 15 to 180 minutes.

The oleum/caprolactam mixture thus obtained is neutralized with ammonia in the conventional manner, and worked up. Suitable processes are described, for example, in Ullmanns Encyklopädie der technischen Chemie, 4th edition, volume 9, page 100.

The process is, for example, carried out in a mixing circuit as shown in FIG. 1.

The mixing circuit 1 comprises a conveying zone 2, a mixing zone 3, a boiling zone 4, including a condenser 5, and a separating zone 6. Oleum or, during the reaction, caprolactam-containing oleum, is circulated through the mixing circuit by pumping. Fresh oleum is introduced through line 7 and cyclohexanone-oxime solution is metered in through line 8 and thoroughly mixed with the circulating mixture in the mixing zone 3. In the boiling zone 4, downstream of the mixing zone 3, the heat of rearrangement is removed by evaporation of the solvent, and the solvent which condenses in the condenser 5 is recycled. In the separating zone 6, the reaction mixture is separated into a solvent phase, the solvent being removed through line 9, and into a caprolactam-containing oleum phase. Caprolactam, dissolved in oleum, is removed from the caprolactam-containing oleum phase through line 10, at the rate at which it is formed.

Caprolactam obtainable by the process of the invention may be used for the preparation of polycaprolactam.

The Example which follows illustrates the process according to the invention.

EXAMPLE

A mixing circuit as shown in the FIGURE is used, comprising the line 1, circulating pump 2, mixing nozzle 3, boiling vessel 4, condenser 5 and separating vessel 6. The liquid volume in the mixing circuit is 8 liters. 60 liters per hour of caprolactam-containing oleum, the caprolactam content being 46% by weight, are circulated by means of the circulating pump 2. 1.695 liters per hour of oleum (containing 28% of $SO_3$) are introduced through line 7, and 14 liters per hour of a 20 percent strength by volume solution of cyclohexanone-oxime in cyclohexane, under a pressure of 17 bar, are introduced through line 8. Under a pressure of 1 bar in the boiling vessel 4, the reaction temperature assumes a value of 80° C., by virtue of the boiling cyclohexane. The content of free sulfur trioxide in the rearrangement mixture is adjusted to 11.9% by weight. In the separating vessel 6, the mixture is separated into two phases and the solvent is taken off through line 9. Caprolactam-containing oleum is taken off through line 10 at the rate at which it is formed. After working up, described in Ullmanns Encyklopädie der technischen Chemie, 4th edition, volume 9, page 100, caprolactam is obtained in a yield of 98.5%. The caprolactam obtained has a UV number of 109, measured in benzene solution, prior to distillation.

UV number

Principle:

The absorption of the caprolactam is measured in the spectral region from 360 to 270 nm and is expressed as a figure of merit after appropriate conversion.

Analytical instruments:

1 recording single-beam spectrophotometer (Carl Zeiss DMR/21), 1 Erlenmeyer flask (200 ml), 2 quartz cells, 10 cm long (layer thickness 10 cm), with cover.

Instructions:

50 mg of caprolactam are dissolved in 50 g of cold doubly distilled water in an Erlenmeyer flask. A cell is filled with this solution up to the calibration mark. The second cell is filled with the same doubly distilled water and represents the comparative solution.

Both cells are now closed with their lids, the ground surfaces are cleaned with tissue paper, and the cells are inserted in the cell holder. The spectrum is then recorded from 370 nm to 260 nm in accordance with the instrument operating manual. The rate of recording is 50 (units). The extinction measurement is effected in the 0–1 measuring range.

When the recording has been completed, a mark is made on the paper at intervals of 10 nm from 270 to 360 nm.

Evaluation:

The extinctions are read off the diagram at 270, 280, 290, 300, 310, 320, 330, 340, 350 and 360 nm, and are added.

The sum of the 10 extinction values is multiplied by 2 and gives the UV number. Accordingly, the UV number is always based on 100% strength caprolactam and on a layer thickness of 10 cm.

We claim:

1. A process for the continuous preparation of ε-caprolactam by Beckmann rearrangement of cyclohexanone-oxime, dissolved in a solvent which is inert towards oleum and is immiscible with oleum and water, at an elevated temperature, with removal of the heat of rearrangement by evaporation of the solvent, wherein oleum containing caprolactam is circulated successively through a conveying zone, a mixing zone, a boiling zone and a separating zone, upstream of the conveying zone oleum is added at the rate at which it is consumed, in the mixing zone cyclohexanone-oxime dissolved in solvent is added under turbulent conditions, in the boiling zone the heat of rearrangement is removed in a conventional manner by evaporating the solvent and recycling the condensate, and in the separating zone the reaction mixture is separated into a solvent phase, from which solvent is withdrawn at the rate at which the phase is formed, and a caprolactam-containing oleum phase, which is removed at the rate at which it is formed.

2. A process as claimed in claim 1, wherein a cyclohexanone-oxime solution of from 10 to 30 percent strength by volume is introduced.

3. A process as claimed in claim 1, wherein the total volume of the caprolactam-containing oleum recycled per unit time is from 3 to 100 times the volume of cyclohexanone-oxime solution introduced.

4. A process as claimed in claim 1, wherein the caprolactam-containing oleum contains from 5 to 15% by weight of free $SO_3$.

5. A process as claimed in claim 1, wherein cyclohexane is used as the solvent.

6. A process as claimed in claim 1, wherein the cyclohexanone-oxime solution is introduced axially and radially through nozzle orifices, under a pressure of from 5 to 25 bar, into a mixing zone which narrows in the axial direction, and caprolactam-containing oleum is introduced laterally into the mixing zone, at the level of the nozzle orifices.

* * * * *